United States Patent [19]

Corbett

[11] 4,374,144
[45] Feb. 15, 1983

[54] β-LACTAM COMPOUNDS, THEIR PREPARATION AND USE

[75] Inventor: David F. Corbett, Dorking, England

[73] Assignee: Beecham Group Limited, England

[21] Appl. No.: 203,509

[22] Filed: Nov. 3, 1980

Related U.S. Application Data

[63] Continuation of Ser. No. 68,890, Aug. 23, 1979, abandoned.

[30] Foreign Application Priority Data

Sep. 9, 1978 [GB] United Kingdom ............... 36266/78

[51] Int. Cl.³ ..................... A61K 31/40; C07D 487/04
[52] U.S. Cl. .............................. 424/274; 260/245.2 T; 424/114
[58] Field of Search ................... 260/245.2 T; 424/274

[56] References Cited

U.S. PATENT DOCUMENTS

| | | | |
|---|---|---|---|
| 4,113,856 | 9/1978 | Cole et al. | 260/245.2 T |
| 4,141,986 | 2/1979 | Cassidy et al. | 260/245.2 T |
| 4,146,610 | 3/1979 | Cole et al. | 260/245.2 T |
| 4,162,323 | 7/1979 | Kahan | 260/245.2 T |
| 4,172,129 | 10/1979 | Cole et al. | 260/245.2 T |
| 4,263,314 | 4/1981 | Ponsford et al. | 260/245.2 T |

FOREIGN PATENT DOCUMENTS 2513854 10/1975 Fed. Rep. of Germany ... 260/245.2 T

OTHER PUBLICATIONS

Merck & Co.; Derwent Abstract 82381y, 4/28/76.
Derwent Abstract 38809, 11/17/76.
Derwent Abstract 33698, 10/13/77.
Maeda et al., J. Antibiotics, vol. 30, p. 770, (1977).
Brown et al., J. Chem. Soc. Chem. Comm., (1977), p. 523-525.

Primary Examiner—Mary C. Lee
Attorney, Agent, or Firm—Jacobs & Jacobs

[57] ABSTRACT

The present invention relates to the preparation of compounds of the formula:

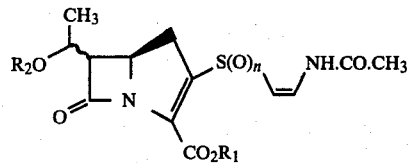

wherein $CO_2R_1$ is a free, salted or esterified carboxyl group, n is 0 or 1, and $R_2$ is hydrogen or an acyl group or a group of the sub-formula (a):

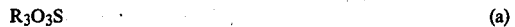

(a)

wherein $R_3$ is a salting ion or a methyl or ethyl group, with the proviso that when $R_2$ is a group of the formula (a), the compound has cis stereochemistry about the α-lactam ring; which have been found to possess antibacterial and α-lactamase inhibitory activity.

62 Claims, No Drawings

β-LACTAM COMPOUNDS, THEIR PREPARATION AND USE

CROSS-REFERENCE

This is a continuation of Ser. No. 68,890 filed Aug. 23, 1979, abandoned.

This invention relates to novel compounds having anti-bacterial and β-lactamase inhibitory activity.

British Pat. Nos. 1489235 and 1467413 disclose that the compounds of the formula (I) and (II):

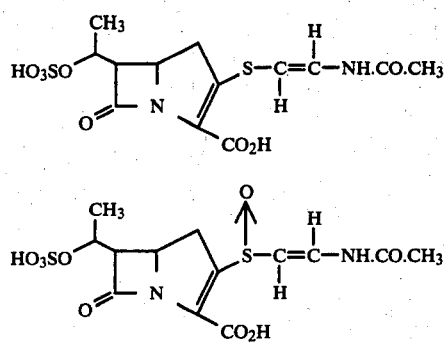

and their salts and esters have anti-bacterial and β-lactamase inhibitory activity.

British Patent Application No. 9366/77 discloses that the compounds of the formula (III):

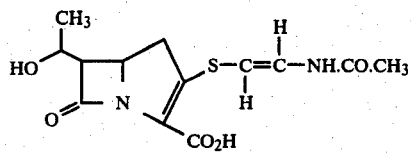

and salts and esters thereof also have anti-bacterial and β-lactamase inhibitory activity.

British Patent Application No.: 16886/78 discloses that compounds of the formula (IV):

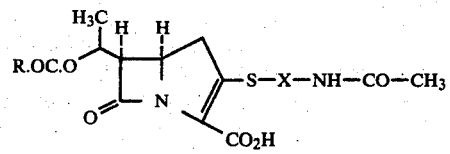

and salts and esters thereof wherein X is a —CH$_2$—CH$_2$— or trans —CH=CH— group and R is a group R$^1$ or NH.R$^1$ wherein R$^1$ is an alkyl group of up to 6 carbon atoms, an alkenyl group of up to 6 carbon atoms, an aryl group or an alkyl group of up to 6 carbon atoms substituted by an aryl or aryloxy group, have antibacterial activity.

British Patent Application No. 18100/78 discloses that compounds of the formulae (V) and (VI):

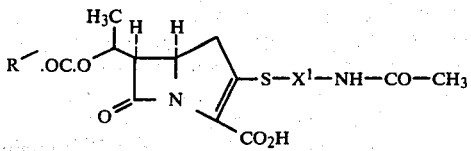

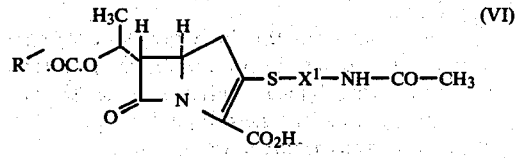

and salts and esters thereof wherein X$^1$ is a —CH$_2$—CH$_2$— or trans —CH=CH— group and

R′ is a group R$^3$ or NH.R$^3$ wherein R$^3$ is an alkyl group of up to 6 carbon atoms, an alkenyl group of up to 6 carbon atoms, an aryl group, or an alkyl group of up to 6 carbon atoms substituted by an aryl or aryloxy group, have anti-bacterial activity.

We have now discovered a further group of compounds which have antibacterial and β-lactamase inhibitory activity.

Accordingly, this invention provides the compounds of the formula (VII):

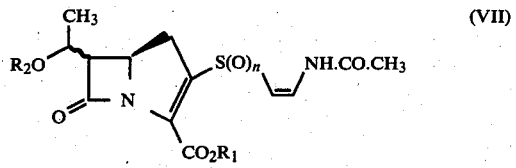

wherein CO$_2$R$_1$ is a free, salted or esterified carboxyl group, n is 0 or 1, and R$_2$ is hydrogen or an acyl group or a group of the sub-formula (a):

$$R_3O_3S \qquad (a)$$

wherein R$_3$ is a salting ion or a methyl or ethyl group, with the proviso that when R$_2$ is a group of the sub-formula (a), the compound has cis stereochemistry about the β-lactam ring.

Preferably, n is 0.

Preferred esterifying groups R$_1$ include lower alkyl, benzyl, substituted benzyl and phthalidyl groups.

Suitable substituted benzyl groups include methyl-, methoxy-, nitro- and halo-benzyl groups, for example, p-nitrobenzyl.

A preferred group of compounds (VII) are those wherein R$_1$ is an alkali or alkaline earth metal ion, for example, sodium or potassium.

One preferred group R$_2$ is a group of the sub-formula (a) wherein R$_3$ is a salting ion as defined for R$_1$ above.

A further preferred group of compounds (VII) are those wherein R$_2$ is a hydrogen atom.

Yet a further preferred group of compounds (VII) are those wherein R$_2$ is an acyl group of the sub-formula R$^4$CO wherein R$_4$ is a group R$_5$ or NH.R$_5$ wherein R$_5$ is an alkyl group of up to 6 carbon atoms, an alkenyl group of up to 6 carbon atoms, an aryl group, or an alkyl group of up to 6 carbon atoms substituted by an aryl or aryloxy group.

When used herein the term "aryl" means a phenyl group or a phenyl group substituted by an alkyl group of up to 3 carbon atoms, an alkoxyl group of up to 3 carbon atoms, a chlorine atom or fluorine atom.

Suitably $R_4$ is a group $NH.R_5$. More suitably $R_4$ is a group $R_5$.

The compounds of this invention when $R_2$ is H or acyl may have either cis or trans stereochemistry about the β-lactam ring. This invention accordingly provides the compounds (VII) where $R_2$ is H or acyl as the cis isomers, the trans isomers, or mixtures of the cis and trans isomers.

This invention also provides a compound of the formula (VII) when in admixture with the corresponding (E)-isomer.

Particularly suitable compounds of this invention include that of the formula (VIII):

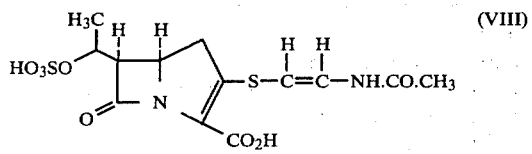

in the form of a pharmaceutically acceptable di-basic salt or of a pharmaceutically acceptable mono-basic of an in-vivo hydrolysable ester of the carboxylate group. Suitable di-basic salts include di-sodium and di-potassium. Suitable mono-salts mono-esters include the sodium and potassium salts of the phthalidyl ester.

The present invention also provides a pharmaceutical composition which comprises a compound of the formula (VII) and a pharmaceutically acceptable carrier therefor.

Suitably the compositions comprise a compound of the formula (VII) in the form of a pharmaceutically acceptable mono- or di-salt.

Suitably the compositions comprise an ester of a compound of the formula (VIII).

The compositions of this invention may be adapted for oral, topical or parenteral administration and may be used for the treatment of bacterial infections in humans or domestic animals such as infections of the respiratory and urinary tracts in humans and mastitis in cattle.

The compositions may be formulated in similar manner to that described in the aforementioned patent applications.

In general unit dosage forms of the compositions will contain from 50 to 500 mg of a compound of this invention, more usually 100 to 300 mg, for example 125, 150, 200 or 250 mg. Such compositions may be administered once or more times a day (usually 3 or 4 times daily) so that the total daily dose is about 300 to 1000 mg for an average adult human.

The compositions of this invention may be used to treat inter alia infections due to *Staphylococcus aureus*, *E.coli* and *Klebsiella aerogenes*.

The compositions described above may have a compound of the invention as sole active ingredient, when that compound is the sole or principal anti-bacterial agent used during treatment.

In addition, the β-lactamase activity of the compounds of the invention renders them particularly useful for concurrent administration with a further β-lactam antibiotic, such as a penicillin or cephalosporin. A composition comprising a compound of the invention may be administered together with a composition comprising the further β-lactam antibiotic, or the two anti-bacterial agents may be administered in a single composition.

Accordingly, this invention further provides a pharmaceutical composition as hereinbefore defined and also comprising a penicillin or cephalosporin.

The ratio of the compound of the invention to penicillin or cephalosporin may be from 10:1 to 1:10 by weight, for example, 3:1 to 1:3.

The penicillin or cephalosporin in unit dose forms of such compositions will be present at about the level normally used in conventional unit dose forms of that penicillin or cephalosporin.

Particularly suitable penicillins for inclusion in such compositions include ampicillin and amoxycillin, and salts and esters thereof, for example the sodium salt or the phthalidyl or pivaloyloxymethyl ester.

Compositions comprising a compound of the invention and a further β-lactam antibiotic may be formulated in a similar manner to those described above.

This invention further provides a process for the preparation of the compounds of the formula (VII), which process comprises the isomerisation of a compound of the formula (VIII):

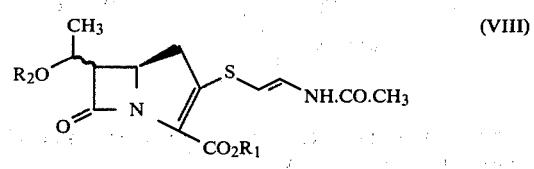

wherein $R_1$ and $R_2$ and the stereochemistry about the β-lactam ring are as defined in relation to formula (VII), by contacting the compound of the formula (VIII) with a mercuric salt in the presence of an inert solvent, and thereafter, if desired carrying out one or both of the following processes:

(a) converting a compound (VII) wherein $R_1$ is a p-nitrobenzyl group to a corresponding compound wherein $R_1$ is a alternative group $R_1$;

(b) oxidising the compound of the formula (VII) wherein n is 0 to produce a corresponding compound wherein n is 1.

The presence of a buffering agent to control the pH of the system has proved advantageous. A suitable agent for this purpose is calcium carbonate.

Preferably, the process of the invention is carried out on a compound (VIII) wherein $R_1$ is an esterifying group, since separation of the corresponding compound (VII) from other materials may then generally be achieved more easily than when the compounds contain a free or salted acid group.

The solvent used in the process will be selected primarily on the basis of the solubility of the compound (VIII) therein, a large number of solvents being suitable; for example, acetonitrile, acetone, dichloromethane, chloroform and water. A suitable solvent mixture is acetonitrile-water.

The reaction is generally carried out at a moderate temperature, for example, from $-30°$ to $+50°$ C., room temperature being particularly convenient, when the reaction is generally complete in a few minutes.

When the compound of the formula (VII) contains no free or salted acid group, it may be isolated from the reaction mixture by extracting it into an organic solvent, washing with aqueous sodium bicarbonate solution, removing the solvent, and subjecting the product to further purification by chromatography.

When the compound of the formula (VII) contains a free or salted acid group, it may be isolated from the reaction mixture by washing an aqueous solution of the product with an organic solvent such as ethyl acetate, removal of the aqueous solvent, and chromatography of the product.

Suitable systems for chromatographic purification of the product include silica gel, using ethyl acetate-petrol or chloroform-ethanol mixtures as eluants.

The conversion of a p-nitrobenzyl group $R_1$ to an alternative group $R_1$ may be achieved by hydrogenolysis, optionally in the presence of a base to form a salt, and optionally thereafter, re-esterifying the resulting free acid or salt, or neutralising a free acid to form a salt.

The hydrogenolysis may be effected using a low, medium or high pressure of hydrogen, slightly superatmospheric pressure being most convenient. Preferably, a transition metal catalyst is present during the hydrogenolysis, for example, palladium on carbon.

The re-esterification of the free acid or salt may be effected by conventional methods, for example, reaction of the acid with a diazo compound, or reaction of a salt with a compound $R_1Z$ where Z is a good leaving group such as Cl, Br, I, $OSO_2CH_3$ or $OSO_2C_6H_4CH_3$, and $R_1$ is a group such that $CO_2R_1$ is an esterified carboxyl group.

Suitable mercuric salts for use in the isomerisation include chloride, bromide, iodide, sulphate and acetate.

Compounds of formula (VII) wherein n is 1 may be prepared from compounds of formula (VII) wherein n is 0 by oxidation with a suitable oxidising agent, such as m-chloroperbenzoic acid, in a suitable solvent, such as dichloromethane or water.

The following Examples illustrate the invention:

EXAMPLE 1

Benzyl (5R, 6S)-3-[(Z)-2-acetamidoethenythio]-6-[(S)-1-hydroxyethyl]-7-oxo-1-azabicyclo[3.2.0]hept-2-ene-2-carboxylate.

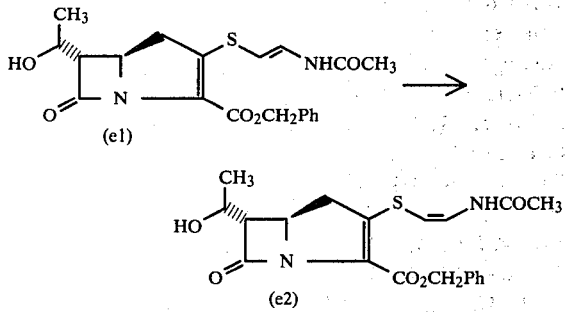

The benzyl ester (e1) (100 mg) was dissolved in a mixture of acetonitrile and water (3:1, 5 ml), and to the solution was added calcium carbonate (50 mg) and mercuric chloride (135 mg). The mixture was stirred at room temperature for 30 min, and ethyl acetate (30 ml) was then added. The organic solution was washed with dilute aqueous sodium bicarbonate solution (20 ml) and brine (20 ml), then dried (MgSO$_4$) and evaporated in vacuo. The residue was chromatographed on silica gel using ethyl acetate followed by 10% ethanol in ethyl acetate to elute.

The first eluted product (30 mg) was benzyl (5R, 6S)-3-[(Z)-2-acetamidoethenylthio]-6-[(S)-1-hydroxyethyl]-7-oxo-1-azabicyclo[3.2.0]hept-2-ene-2-carboxylate (e2); $\lambda_{max}$(EtOH) 325 and 230 nm.; $\gamma_{max}$(CHCl$_3$) 1780, 1700 and 1630 cm$^{-1}$; $\delta$(CDCl$_3$) 1.31 (3H, d, J 6 Hz, CH$_3$CH), 2.05 (3H, s, CH$_3$CO), 2.45 (1H, br, s, OH), 2.87 (1H, dd, J 9 and 18 Hz, H$_A$ of ABX, 4-CH), 3.11 (1H, dd, J 9 and 18 Hz, H$_B$ of ABX, 4-CH), 3.21 (1H, dd, J 3 and 5 Hz, 6-CH), 3.90-4.25 (2H, m, 5-CH and CH$_3$CH), 5.28 (2H, centre of AB, wings at 5.13 and 5.42, CH$_2$Ph), 5.32 (1H, d, J 8 Hz, CH=CH.S), 7.25-7.55 (6H, m, CH=CH.N and PhCH$_2$) and 8.11 (1H, d, J 11 Hz, NH). INDOR spectrum of resonance at $\delta$5.32 reveals $\delta$7.35 (dd, J 8 and 11 Hz, CH=CHNH).

EXAMPLE 2 p-Nitrobenzyl (5R, 6S)-3-[(Z)-2-acetamidoethenylthio]-6-[(S)-1-hydroxyethyl]-7-oxo-1-azabicyclo[3.2.0]hept-2-ene-2-carboxylate.

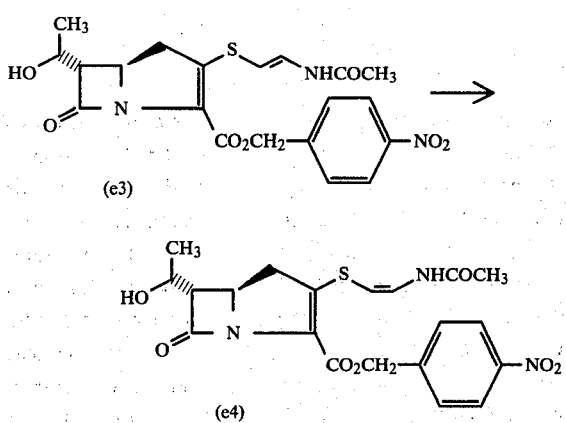

The ester (e3) (430mg) was dissolved in CH$_3$CN/H$_2$O (3:1, 20ml), and to the solution was added CaCO$_3$ (115mg) and HgCl$_2$ (261mg). After stirring for 30 min. at room temperature, ethyl acetate (50ml) was added. The organic solution was shaken with dilute NaHCO$_3$ solution (2×25ml) and brine (30ml), then dried (MgSO$_4$) and evaporated in vacuo. The residue was chromatographed on silica gel using a gradient elution with CHCl$_3$ to 20% EtOH in CHCl$_3$.

The first eluted product was p-nitrobenzyl (5R, 6S)-3-[(Z)-2-acetamidoethenylthio]-6-[(S)-1-hydroxyethyl]-7-oxo-1-azabicyclo[3.2.0]hept-2-ene-2-carboxylate (e4), which was obtained as a pale yellow solid (135mg) by trituration with ether; m.p. 158°-160°;$\lambda_{max}$ (EtOH) 326 (14,020), 263 (15,848) and 235 nm (14,020);$\gamma_{max}$ (KBr) 1775, 1690 and 1630 cm$^{-1}$; $\delta$(DMF-d$_7$) 1.27 (3H, d, J 6.5Hz, CH$_3$CH), 2.10 (3H, s, CH$_3$CO), ca. 3.25 (2H, centre of m, 4-CH$_2$), ca. 3.5 (1H, m, 6-CH), 3.95-4.35 (2H, m, 5-CH and CH$_3$CH), 5.16 (1H, d, J 5Hz, OH), 5.33 and 5.60 (each 1H, d, J 14Hz, CH$_2$Ar), 5.65 (1H, d, J 8Hz, SCH=CH), 7.25 (1H, approx dd, J 8 and 11Hz, collapses to d, J, 8Hz, on addition of D$_2$O, CH=CH.NH), 7.82 and 8.25 (each 2H, d, J 8.5Hz, Ar CH$_2$) and ca. 10.0 (1H, br, NH).

EXAMPLE 3

Sodium (5R, 6S)-3-[(Z)-2-acetamidoethenylthio]-6-[(S)-1-hydroxyethyl]-7-oxo-1-azabicyclo[3.2.0]hept-2-ene-2-carboxylate.

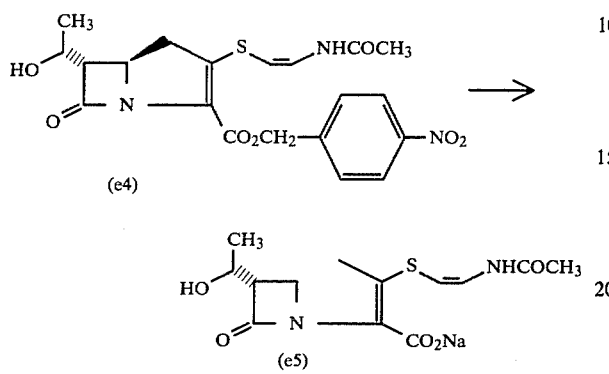

A mixture of 5% Pd on C (100mg) and 30% aqueous dioxan (8ml) was hydrogenated for 0.5 hr. A solution of the ester (e4) (100mg) in 30% aqueous dioxan (2ml) was added to the catalyst mixture, and hydrogenation continued for 4 hr at 1 atmosphere and room temperature.

A solution of NaHCO$_3$ (19mg) in water (2ml) was added to the mixture which was filtered through Celite, washing it well with water (15ml). The solution was concentrated in vacuo to a volume of ca. 10ml, and then washed with ethyl acetate (3×30ml). The aqueous layer was further concentrated to ca. 5ml, and then passed through a column (20×2.5cm) of Biogel P2, eluting with deionised water. Fractions containing the product, as determined by uv, were combined and evaporated in vacuo. Water was azeotroped off with ethanol, and ethanol with toluene to afford sodium (5R,6S)-3-[(Z)-2-acetamidoethenylthio]-6-[(S)-1-hydroxyethyl]-7-oxo-1-azabicylo[3.2.0]hept-2-ene-2-carboxylate (e5) as a yellow solid. (48mg);$\lambda_{max}$ (H$_2$O) 305 and 229 nm;$\gamma_{max}$ (KBr) 1755, 1675, and 1620 cm$^{-1}$;$\delta$(D$_2$O) inter alia 1.26 (3H, d, J 6Hz, (C$\underline{H}_3$CH), 2.08 (3H, s, C$\underline{H}_3$CO), 3.05 (2H, centre of m, 4-C$\underline{H}_2$), 3.40 (1H, m 6-C$\underline{H}$), ca. 4.1 (2H, m, 5-C$\underline{H}$ and C$\underline{H}$CH$_3$), 5.60 (1H, d, J 7.5 Hz, CH=C$\underline{H}$.S) and 7.04 (1H, d, J 7.5 Hz, CH=C$\underline{H}$N).

The sodium salt of the (Z)-isomer (e5) was examined by h.p.l.c* and showed a single peak with a retention time of 11.3 minutes. The sodium salt of the corresponding (E)-isomer under the same conditions possessed a retention time of 7.0 minutes.

*High pressure liquid chromatography (h.p.l.c) was used under the following conditions:

Column: 300 mm×3.9 mm filled with μ-bondapack C18 (Waters Associates, Milford, Massachussets, U.S.A).

Solvent: 0.05 M ammonium phosphate, adjusted to pH 7 with ammonia, in 5% acetonitrile—95% water.

Flow rate: 2.0 ml per minute

Detection: UV absorbance at 305 nm.

Load: 10μl of a solution of ca. 1 mg per ml.

EXAMPLE 4 p-Nitrobenzyl (5R, 6R)-3-[(Z)-2-acetamidoethenylthio]-6-[(S)-1-hydroxyethyl]-7-oxo-1-azabicyclo[3.2.0]hept-2-ene-2-carboxylate.

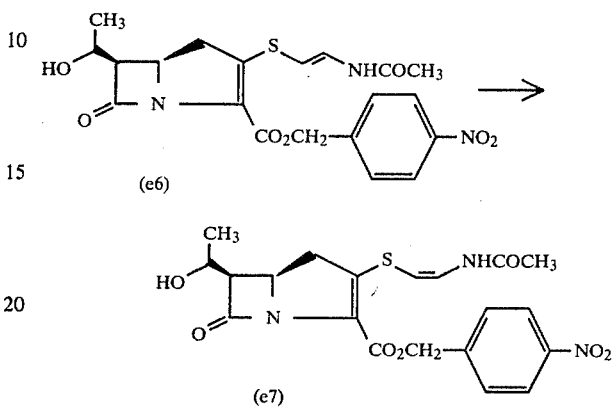

A solution of the p-nitrobenzyl ester (e6) (257 mg) in 30% aqueous acetonitrile (10 ml) was treated with calcium carbonate (62 mg) and mercuric chloride (110 mg). After stirring at r.t. for 30 min. the mixture was filtered and then diluted with ethyl acetate (30 ml). The organic solution was washed with dilute aqueous sodium bicarbonate solution (20 ml×2) and brine (20 ml). Evaporation of the dried (MgSO$_4$) solution gave a product which was chromatographed on silica gel using a gradient elution from CHCl$_3$ to 20% EtOH in CHCl$_3$.

The first eluted product was p-nitrobenzyl (5R, 6R)-3-[(Z)-2-acetamidoethenylthio]-6-[(S)-1-hydroxyethyl]-7-oxo-1-azabicyclo[3.2.0]hept-2-ene-carboxylate (e7), obtained as a pale-yellow amorphous solid (133mg),$\lambda_{max}$ (EtOH) 325, 263 and 233 nm; $\gamma_{max}$ (CHCl$_3$) 1775, 1730 and 1630 cm$^{-1}$;$\delta$(CDCl$_3$) 1.38 (3H, d, J 6Hz, C$\underline{H}_3$CH), 2.10 (3H, s, C$\underline{H}_3$CO), 2.25 (1H, br, O$\underline{H}$), 3.01 (1H, dd, J 18 and 10 Hz, H$_A$ of ABX, 4-C$\underline{H}$), 3.43 (1H, dd, J 18 and 9Hz, H$_B$ of ABX, 4-C$\underline{H}$), 3.60 (1H, dd, J 5.5 and 9 Hz, 6-C$\underline{H}$), 4.0-4.45 (2H, m, 5-C$\underline{H}$ and 8-C$\underline{H}$), 5.40 (1H, d, J 8 Hz, CH=C$\underline{H}$.S), 5.21 and 5.48 (each 1H, d, J 15 Hz, C$\underline{H}_2$Ar), 7.33 (1H, dd, J 8 and 11 Hz, CH=C$\underline{H}$.NH), 7.62 and 8.20 (each 2H, d, J 8Hz, CH$_2$Ar) and 7.91 (1H,br d, J 11 Hz, N$\underline{H}$).

EXAMPLE 5

Sodium (5R, 6R)-3-[(Z)-2-acetamidoethenylthio]-6-[(S)-1-hydroxyethyl]-7-oxo-1-azabicyclo[3.2.0]hept-2-ene-2-carboxylate.

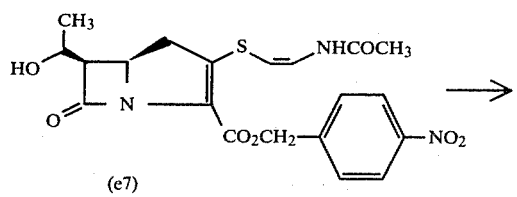

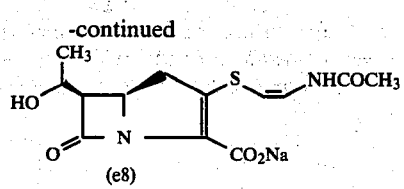

5% Pd on C (100 mg) was hydrogenated in 20% aqueous dioxan (8 ml) for 0.5 hr. A solution of the ester (e7) (100 mg) in 20% aqueous dioxan (2 ml) was added to the mixture and hydrogenation was continued for 4 hr. A solution of NaHCO$_3$ (19 mg) in water (5 ml) was added, and the mixture was filtered over Celite, washing well with water (15 ml). The aqueous solution was concentrated in vacuo to a volume of ca. 10 ml. and then was washed with ethyl acetate (3×30 ml). Further evaporation of the aqueous solution to ca. 5 ml followed by chromatography on Biogel P2 eluting with water gave several fractions which contained the required chromophore in the UV (305nm). These were combined and evaporated in vacuo, azeotroping out the water with ethanol, and the ethanol with toluene to afford a cream coloured solid (25 mg) which consisted of sodium (5R, 6R)-3-[(Z)-2-acetamidoethenyl-thio]-6-[(S)-1-hydroxyethyl]-7-oxo-1-azabicyclo[3.2.0]hept-2-ene-2-carboxylate (e8);$\lambda_{max}$ (H$_2$O) 305 and 232 nm;$\gamma_{max}$ (KBr) 1750, 1675 and 1600–1625(br)cm$^{-1}$.

H.p.l.c* of the product showed a single peak with a retention time of 7.7 min, whilst the corresponding (E)-isomer had a retention time of 6.2 min.

EXAMPLE 6 p-Nitrobenzyl (5R, 6R)-3-[(Z)-2-acetamidoethenylthio]-6-[(S)-1-ethoxysulphonyloxyethyl]-7-oxo-1-azabicyclo[3.2.0]hept-2-ene-2-carboxylate.

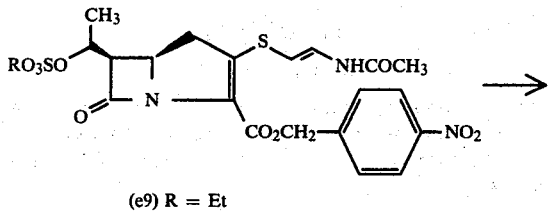

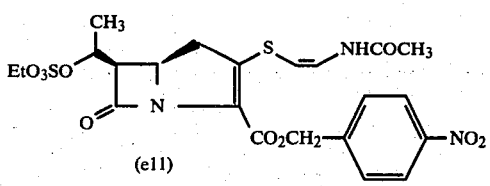

A crude sample of diester (e9) [prepared from the quartenary ammonium salt (e10) (305mg) and Meerweins reagent (76mg)] was dissolved in 30% aqueous acetonitrile (10ml). The solution was treated with mercuric chloride (56mg) at room temperature for 20 min. The solution was concentrated in vacuo, and the residue partitioned between ethyl acetate and water. The organic layer was washed with dilute NaHCO$_3$ solution and brine, then dried (MgSO$_4$) and evaporated in vacuo. The residue was chromatographed on silica gel using a gradient elution from 50% cyclohexane in ethyl acetate to ethyl acetate.

The first eluted product was p-Nitrobenzyl (5R, 6R)-3-[(Z)-2-acetamidoethenylthio]-6-[(S)-1-ethoxysulphonyloxyethyl]-7-oxo-1-azabicyclo[3.2.0]hept-2-ene-2-carboxylate (e11) (45mg);$\gamma_{max}$ (CHCl$_3$) 1780, 1705 and 1630cm$^{-1}$; $\delta$(CDCl$_3$) 1.40 (3H, t, J 7Hz, C$\underline{H}_3$CH$_2$), 1.65 (3H, d, J 6.5Hz, C$\underline{H}_3$CH),2.09 (3H, s, C$\underline{H}_3$CO), ca. 3.2 (2H, centre of m, 4-CH$_2$) 3.84 (1H, dd, J 5.5 and 9.5 Hz, 6-C$\underline{H}$), ca. 4.05–4.5 (3H, m, 5-C$\underline{H}$ and OC$\underline{H}_2$CH$_3$), ca. 5.0 (1H, m, CHC$\underline{H}_3$) 5.22 and 5.49 (each 1H, d, J 14Hz, C$\underline{H}_2$Ar), 5.38 (1H, d, J 8Hz, CH=C$\underline{H}$S), ca. 7.40 (1H, dd, J 8 and 11 Hz, CH=C$\underline{H}$NH), 7.60 and 8.21 (each 2H, d, J 9Hz, ArCH$_2$) and ca. 7.8 (1H,br d, N$\underline{H}$).

EXAMPLE 7 p-Nitrobenzyl (5R, 6R)-3-[(Z)-2-acetamidoethenylthio]-6-[(S)-1-sodiosulphatoethyl]-7-oxo-1-azabicyclo[3.2.0]hept-2-ene-2-carboxylate.

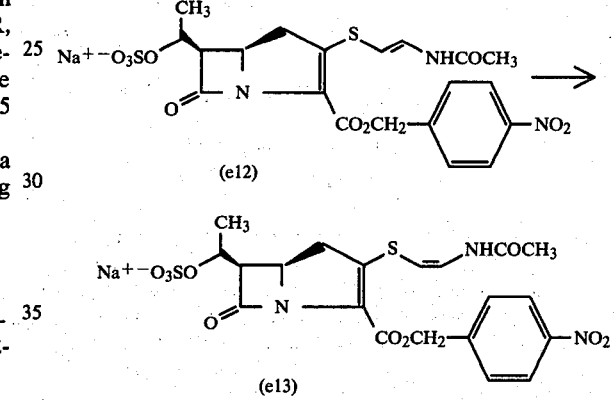

The mono-p-nitrobenzyl ester mono-sodium salt (e12) (390 mg) was dissolved in 30% aqueous acetonitrile (15 ml) and to the solution was added CaCO$_3$ (72 mg) and HgCl$_2$ (100mg). The mixture was stirred at room temperature for 45 min. and then filtered. The solution was diluted with water (15 ml) and the aqueous layer was washed with ethyl acetate (2×50ml). Acetonitrile was added to the aqueous solution which was then evaporated in vacuo, adding more acetonitrile as necessary until all the water had been removed.

The residue was chromatographed on silica gel using 30% EtOH in CHCl$_3$ as eluant to afford separation of the two components. The first product, obtained as a pale yellow solid (96 mg) was p-nitrobenzyl (5R, 6R)-3-[(Z)-2-acetamidoethenylthio]-6-[(S)-1-sodiosulphatoethyl]-7-oxo-1-azabicyclo[3.2.0]hept-2-ene-2-carboxylate (e13);$\lambda_{max}$(H$_2$O) 320, 265 and 230 nm; $\gamma_{max}$(KBr) 1770, 1690 and 1625cm$^{-1}$. $\delta$(DMSO-d$_6$) 1.37 (3H, d, J 6Hz, C$\underline{H}_3$CH), 2.00 (3H, s, C$\underline{H}_3$CO), 2.8–3.65 (2H, m, 4-C$\underline{H}_2$), 3.70 (1H, dd, J 6 and 11Hz, 6-C$\underline{H}$), 4.0–4.55 (2H, m, 5-C$\underline{H}$ and CH$_3$C$\underline{H}$), 5.25 and 5.45 (each 1H, d, J 13Hz, C$\underline{H}_2$Ar), 5.42 (1H, d, J 8Hz, CH=C$\underline{H}$.S), 7.10 (1H, dd, J 8 and 11Hz, CH=C$\underline{H}$NH), 7.68 and 8.19 (each 2H, d, J 9Hz, aromatic protons) and 9.76 (1H, d, J 11Hz, N$\underline{H}$).

EXAMPLE 8

Disodium (5R, 6R)-3-[(Z)-2-acetamidoethenylthio]-6-[(S)-1-sulphatoethyl]-7-oxo-1-azabcicyclo[3.2.0]hept-2-ene-2-carboxylate.

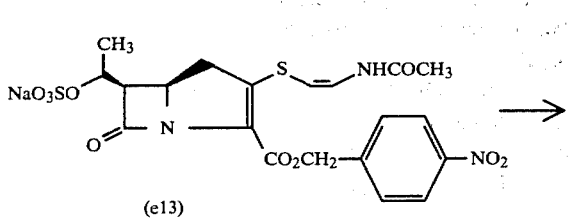

(e13)

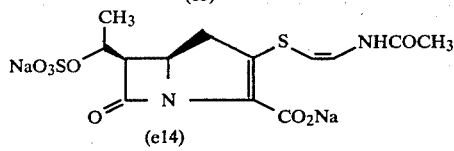

(e14)

5% Pd on C (80 mg) was hydrogenated in 30% aqueous dioxan (7 ml) for 0.5 h. A solution of the ester (e13) (70 mg) in 30% aqueous dioxan (3 ml) was introduced into the hydrogenation vessel, and hydrogenation was continued for 4 h. A solution of NaHCO$_3$ (12 mg) in water (3 ml) was added to the mixture, which was then filtered over Celite, washing well with water (15 ml). The solution was concentrated in vacuo to ca. 10 ml and then washed with ethyl acetate (3×25 ml).

The aqueous layer was concentrated to ca. 5 ml and then chromatographed on Biogel P2 eluting with water. Fractions were monitored by UV and these containing a chromophore at 304 nm were combined and evaporated in vacuo. Further evaporation of ethanol and then toluene from the product afforded disodium (5R, 6R)-3-[(Z)-2-acetamidoethenylthio]-6-[(S)-1-sulphatoethyl]-7-oxo-1-azabicyclo[3.2.0]hept-2-ene-2-carboxylate (e14) as a pale yellow solid (26mg); $\lambda_{max}$ (H$_2$O) 304 and 232 nm; $\gamma_{max}$ (KBr) 1750, 1675 and 1620cm$^{-1}$.

H.p.l.c* of the product (e14) showed a single trace with a retention time of 4.7 min compared to 5.7 min for the disodium salt of the corresponding (E)-isomer.

EXAMPLE 9

Disodium (5R, 6R)-3-[(Z)-2-acetamidoethenylthio]-6-[(S)-1-sulphatoethyl]-7-oxo-1-azabicyclo[3.2.0]hept-2-ene-2carboxylate.

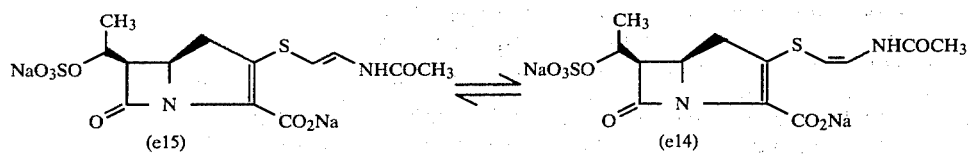

(A) A solution of the disodium salt (e15) (1mg) in 50% aqueous acetonitrile (1ml) was treated with a trace of HgCl$_2$ for 30 min at room temperature. The solution was examined by h.l.p.c* which showed the presence of the (E)-isomer (e15) and the (Z)-isomer (e14) in a ratio of ca. 1:1.1.

(B) The disodium salt of the (Z)-isomer (e14) (1mg) was dissolved in 50% aqueous acetonitrile, and to the solution was added mercuric chloride (trace). After 30 min., h.p.l.c* showed the presence of two peaks corresponding to the (E)-isomer (e15) and the (Z)-isomer (e14) (ca. 1:1.3).

EXAMPLE 10 p-Nitrobenzyl (5R, 6S)-3-[(Z)-2-acetamidoethenylthio]-6-[(S)-1-hydroxyethyl]-7-oxo-1-azabicyclo[3.2.0]hept-2-ene-2-carboxylate, and corresponding (E)-isomer.

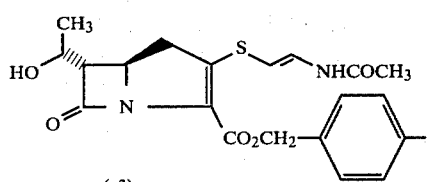

(e3)

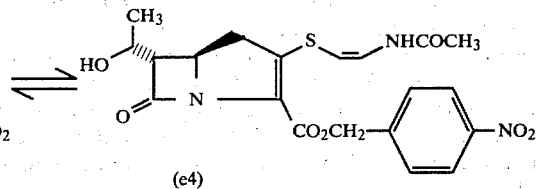

(e4)

(A) The (Z)-isomer (e4) (1 mg) was dissolved in 30% aqueous acetonitrile (1 ml) and to the solution was added a trace of mercuric chloride. After 15 min the solution was examined by t.l.c. (silica gel plate; ethyl acetate as eluant), which showed the presence of a mixture of the (Z)-isomer (e4) and the (E)-isomer (e3).

(B) Solutions of the (E)-isomer (e3) (ca. 1 mg) in 30% aqueous acetonitrile (0.5 ml) were treated with (a) mercuric sulphate (b) mercuric iodide (c) mercuric acetate and (d) mercuric bromide, respectively. In each case, examination of the solution by t.l.c. after 15 min showed the presence of both the (E)-isomer (e3) and the (Z)-isomer (e4).

Demonstration 1

Antibacterial Activity

The minimum inhibitory concentrations (MIC) of certain compounds of the invention were determined against a range of organisms. The results are shown below.

| Organism | MIC (µg/ml) Compound of Example No: | | | |
|---|---|---|---|---|
| | 2 | 3 | 8 | 5 |
| Citrobacter freundii E8 | 5.0 | 2.5 | 1.2 | 1.0 |
| E. coli 0111 | 2.5 | 5.0 | 1.2 | 1.0 |
| E. coli JT39 | >50 | 10 | 2.5 | 10 |
| Klebsiella aerogenes A | 2.5 | 5.0 | 0.5 | 1.0 |
| Proteus mirabilis C977 | 5.0 | 25 | 1.2 | 1.0 |
| Salmonella typhimurium CT10 | 2.5 | 5.0 | 1.2 | 1.0 |
| Shigella sonnei | | | | |

| | MIC (μg/ml) Compound of Example No: | | | |
|---|---|---|---|---|
| Organism | 2 | 3 | 8 | 5 |
| MB11967 | 2.5 | 10 | 1.2 | 1.0 |
| *Bacillus subtilis* A | 0.5 | 5.0 | 1.2 | 0.1 |
| *Staph. aureus* Oxford | 0.5 | 0.5 | 1.2 | 0.2 |
| *Staph. aureus* Russell | 1.2 | 0.5 | 1.2 | 0.5 |
| *Streptococcus pyogenes* CN10 | ≦0.1 | 0.5 | 0.2 | ≦0.02 |

(MIC's were determined using DST agar + 10% horse blood, with an inoculum of 0.001 ml of a $10^{-2}$ dilution for Gram-positive bacteria or a $10^{-4}$ dilution for Gram-negative bacteria).

Demonstration 2

β-Lactamase Inhibitory Activity $I_{50}$ values for certain compounds of the invention against various β-lactamases were determined as follows:

Enzyme (0.2 ml) and inhibitor solution (10 μl) were incubated at pH 7.3, 37° C. for 5 minutes. Substrate (0.2 ml), which was the chromogenic cephalosporin described by O'Callaghan, Morris, Kirby and Shingler, Antimicrobial Agents and Chemotherapy, vol. 1, no. 4, 283–288 (1972), was added to give a final concentration of 250 μg/ml. After a further five minutes (37° C. at pH 7.3) the reaction was diluted with 1.6 ml of water and absorbance at 482 nm recorded instantly. The enzyme level was sufficient to hydrolyse 75% of the substrate in 5 minutes. Levels of inhibition were measured against a control reaction with no added inhibitor (10 μl buffer). $I_{50}$ values quoted are the concentrations required to give 50% inhibition of substrate hydrolysis under the conditions described and are the concentrations of inhibitor present with the enzyme prior to the addition of the substrate.

The results are shown below.

| | $I_{50}$ (μg/ml) β-Lactamase from | | | |
|---|---|---|---|---|
| Compound of Example No: | *Enterobacter cloacae* P99 | *Klebsiella aerogenes* E70 | *E. coli* JT4 | *Staphylococcus aureus* Russell |
| 3 | 0.006 | 0.1 | 0.05 | ca. 3.0 |
| 8 | 0.003 | 0.01 | 0.1 | 0.25 |

What we claim is:

1. A compound of the formula (VII):

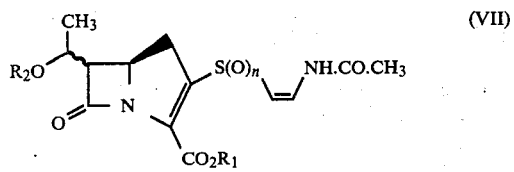

(VII)

wherein CO₂R₁ is carboxylic acid, a pharmaceutically acceptable salt thereof or a pharmaceutically acceptable ester thereof, n is 0 and R₂ is hydrogen, or a group of the sub-formula (a):

(a)

wherein R₃ is a pharmaceutically acceptable salting ion, methyl or ethyl, or a group of the sub-formula (b):

(b)

wherein R₄ is R₅ or NHR₅ wherein R₅ is alkyl of up to 6 carbon atoms, alkenyl of up to 6 carbon atoms, phenyl unsubstituted or substituted by alkyl of up to 3 carbon atoms, alkoxyl of up to 3 carbon atoms, chlorine or fluorine or alkyl of up to 6 carbon atoms substituted by phenyl or phenyloxy which itself is unsubstituted or nuclear substituted by alkyl of up to 3 carbon atoms, alkoxyl of up to 3 carbon atoms, chlorine or fluorine, with the proviso that when R₂ is a group of the formula (a) the compound has cis stereochemistry about the β-lactam ring.

2. A compound according to claim 1 wherein R₁ is lower alkyl, benzyl, methylbenzyl, methoxybenzyl, nitrobenzyl, halobenzyl or phthalidyl.

3. A compound according to claim 1 wherein R₁ is an alkali or alkaline earth metal ion.

4. A compound according to claim 1 wherein R₂ is a group of the sub-formula (a) when R₃ is an alkali or alkaline earth metal ion.

5. A compound according to claim 1 wherein R₂ is hydrogen.

6. A compound according to claim 1 wherein R₂ is of the sub-formula (b):

(b)

wherein R₄ is a group R₅ or NHR₅ wherein R₅ is alkyl of up to 6 carbon atoms, alkenyl of up to 6 carbon atoms, phenyl unsubstituted or substituted by alkyl of up to 3 carbon atoms, alkoxy of up to 3 carbon atoms, chlorine or fluorine, or alkyl of up to 6 carbon atoms substituted by phenyl or phenyloxy which is unsubstituted or nuclear substituted by alkyl of up to 3 carbon atoms, alkoxyl of up to 3 carbon atoms, chlorine or fluorine.

7. A compound according to claim 1 wherein the compound is of the formula (VIII):

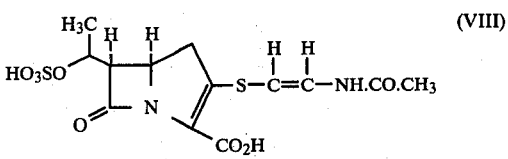

(VIII)

in the form of a pharmaceutically acceptable di-basic salt or of a pharmaceutically acceptable mono-basic salt of an in-vivo hydrolysable ester of the carboxylate group.

8. A compound according to claim 6 wherein R₄ is NH.R₅ wherein R₅ is alkyl of up to 6 carbon atoms, alkenyl of up to 6 carbon atoms, phenyl unsubstituted or substituted by alkyl of up to 3 carbon atoms, alkoxyl of up to 3 carbon atoms, chlorine or fluorine, or alkyl of up to 6 carbon atoms substituted by phenyl or phenyloxy which is unsubstituted or nuclear substituted by alkyl of up to 3 carbon atoms, alkoxyl of up to 3 carbon atoms, chlorine or fluorine.

9. A compound according to claim 6 wherein R₄ is R₅ wherein R₅ is alkyl of up to 6 carbon atoms, alkenyl of up to 6 carbon atoms, phenyl unsubstituted or substituted by alkyl of up to 3 carbon atoms, alkoxyl of up to 3 carbon atoms, chlorine or fluorine, or alkyl of up to 6 carbon atoms substituted by phenyl or phenyloxy which is unsubstituted or nuclear substituted by alkyl of up to 3 carbon atoms, alkoxyl or up to 3 carbon atoms, chlorine or fluorine.

10. A salt according to claim 7 wherein the di-basic salt is the di-sodium or di-potassium salt and the mono-salt of an in-vivo hydrolysable ester is the sodium or potassium salt of the phthalidyl ester.

11. The compound according to claim 1 which is benzyl (5R,6S)-3-[(Z)-2-acetamidoethenylthio]-6-[(S)-1-hydroxyethyl]-7-oxo-1-azabicyclo[3.2.0]hept-2-ene-2-carboxylate.

12. The compound according to claim 1 which is p-nitrobenzyl (5R,6S)-3-[(Z)-2-acetamidoethenylthio]-6-[(S)-1-hydroethyl]-7-oxo-1-azabicyclo[3.2.0]hept-2-ene-2-carboxylate.

13. The compound according to claim 1 which is sodium (5R,6S)-3-[(Z)-2-acetamidoethenylthio]-6-[(S)-1-hydroxyethyl]-7-oxo-1-azabicyclo[3.2.0]hept-2-ene-2-carboxylate.

14. The compound according to claim 1 which is p-nitrobenzyl (5R,6S)-3-[(Z)-2-acetamidoethenylthio]-6-[(S)-1-hydroxyethyl]-7-oxo-1-azabicyclo[3.2.0]hept-2-ene-2-carboxylate.

15. The compound according to claim 1 which is sodium (5R,6R)-3-[(Z)-2-acetamidoethenylthio]-6-[(S)-1-hydroxyethyl]-7-oxo-1-azabicyclo[3.2.0]-hept]2]ene-2-carboxylate.

16. The compound according to claim 1 which is p-nitrobenzyl (5R,6R)-3-[(Z)-2-acetamidoethenylthio]-6-[(S)-1-ethoxysulphonyloxyethyl]-7-oxo-1-azabicyclo[3.2.0]hept-2-ene-2-carboxylate.

17. The compound according to claim 1 which is p-nitrobenzyl (5R,6R)-3-[(Z)-2-acetamidoethenylthio]-6-[(S)-1-sodiosulphatoethyl]-7-oxo-1-azabicyclo[3.2.0-]hept-2-ene-2-carboxylate.

18. The compound according to claim 1 which is disodium (5R,6R)-3-[(Z)-2-acetamidoethenylthio]-6-[(S)-1-sulphatoethyl]-7-oxo-1-azabicyclo[3.2.0]hept-2-ene-2-carboxylate.

19. A pharmaceutical composition useful for treating bacterial infections in humans and animals which comprises an antibacterially effective amount of a compound of the formula (VII):

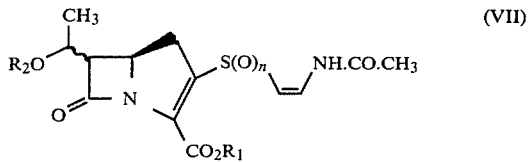

wherein $CO_2R_1$ is carboxylic acid, a pharmaceutically acceptable salt thereof or a pharmaceutically acceptable ester thereof, n is O and $R_2$ is hydrogen, a group of the sub-formula (a):

wherein $R_3$ is a pharmaceutically acceptable salting ion, methyl or ethyl, or a group of the sub-formula (b):

wherein $R_4$ is $R_5$ or $NHR_5$ is alkyl of up to 6 carbon atoms, alkenyl of up to 6 carbon atoms, phenyl unsubstituted or substituted by alkyl of up to 3 carbon atoms, alkoxyl of up to 3 carbon atoms, chlorine or fluorine or alkyl of up to 6 carbon atoms substituted by phenyl or phenyloxy which itself is unsubstituted or nuclear substituted by alkyl of up to 3 carbon atoms, alkoxyl of up to 3 carbon atoms, chlorine or fluorine, with the proviso that when $R_2$ is a group of the formula (a) the compound has cis stereochemistry about the β-lactam ring, in combination with a pharmaceutically acceptable carrier.

20. A composition according to claim 19 wherein $R_1$ is lower alkyl, benzyl, methylbenzyl, methoxybenzyl, nitrobenzyl, halobenzyl or phthalidyl.

21. A composition according to claim 19 wherein $R_1$ is an alkali or alkaline earth metal ion.

22. A composition according to claim 19 wherein $R_2$ is a group of the sub-formula (a) when $R_3$ is an alkali or alkaline earth metal ion.

23. A composition according to claim 19 wherein $R_2$ is hydrogen.

24. A composition according to claim 19 wherein the compound is of the formula (VIII):

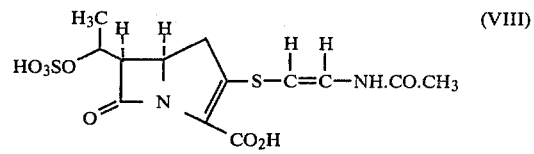

in the form of a pharmaceutically acceptable di-basic salt or of a pharmaceutically acceptable mono-basic salt of an in-vivo hydrolysable ester of the carboxylate group.

25. A composition according to claim 19 wherein $R_4$ is $R_5$ wherein $R_5$ is alkyl of up to 6 carbon atoms, alkenyl of up to 6 carbon atoms, phenyl unsubstituted or substituted by alkyl of up to 3 carbon atoms, alkoxyl of up to 3 carbon atoms, chlorine or fluorine, or alkyl of up to 6 carbon atoms substituted by phenyl or phenyloxy which is unsubstituted or nuclear substituted by alkyl of up to 3 carbon atoms, alkoxyl of up to 3 carbon atoms, chlorine or fluorine.

26. A composition according to claim 24 wherein the di-basic salt is the di-sodium or di-potassium salt and the mono-salt of an in-vivo hydrolysable ester is the sodium or potassium salt of the phthalidyl ester.

27. A composition according to claim 19 wherein the compound is: benzyl (5R,6S)-3-[(Z)-2-acetamidoethenylthio]-6-[(S)-1-hydroxyethyl]-7-oxo-1-azabicyclo[3.2.0]hept-2-ene-2-carboxylate.

28. A composition according to claim 19 wherein the compound is: p-nitrobenzyl (5R,6S)-3-[(Z)-2-acetamidoethenylthio]-6-[(S)-1-hydroxyethyl]-7-oxo-1-azabicyclo[3.2.0]hept-2-ene-2-carboxylate.

29. A composition according to claim 19 wherein the compound is sodium (5R,6S)-3-[(Z)-2-acetamidoethenylthio]-6-[(S)-1-hydroxyethyl]-7-oxo-1-azabicyclo[3.2.0]hept-2-ene-2-carboxylate.

30. A composition according to claim 19 wherein the compound is p-nitrobenzyl (5R,6R)-3-[(Z)-2-acetamidoethenylthio]-6-[(S)-1-hydroxyethyl]-7-oxo-1-azabicyclo[3.2.0]hept-2-ene-2-carboxylate.

31. A composition according to claim 19 wherein the compound is sodium (5R,6R)-3-[(Z)-2-acetamidoethenylthio]-6-[(S)-1-hydroxyethyl]-7-oxo-1-azabicyclo[3.2.0]hept]2]ene-2-carboxylate.

32. A composition according to claim 19 wherein the compound is p-nitrobenzyl (5R,6R)-3-[(Z)-2-acetamidoethenylthio]-6-[(S)-1-ethoxysulphonyloxyethyl]-7-oxo-1-azabicyclo[3.2.0]hept-2-ene-2-carboxylate.

33. A composition according to claim 19 wherein the compound is p-nitrobenzyl (5R,6R)-3-[(Z)-2-acetamidoethenylthio]-6-[(S)-1-sodiosulphatoethyl]-7-oxo-1-azabicyclo[3.2.0]hept-2-ene-2-carboxylate.

34. A composition according to claim 19 wherein the compound is disodium (5R,6R)-3-[(Z)-2-acetamidoethenylthio]-6-[(S)-1-sulphatoethyl]-7-oxo-1-azabicyclo[3.2.0]hept-2-ene-2-carboxylate.

35. A composition according to claim 19 in oral administration form.

36. A composition according to claim 19 in parenteral administration form.

37. A composition according to claim 19 in a form suitable for topical application.

38. A method of treating bacterial infections in humans and animals which comprises administering to a human or animal in need thereof an antibacterially effective amount of a compound of the formula (VII):

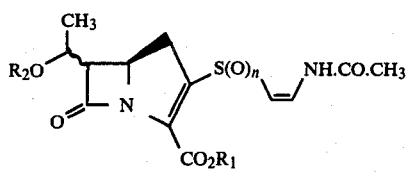

wherein $CO_2R_1$ is carboxylic acid, a pharmaceutically acceptable salt thereof or a pharmaceutically acceptable ester thereof, n is 0 and $R_2$ is hydrogen, a group of the sub-formula (a):

$$R_3O_3S \qquad (a)$$

wherein $R_3$ is a pharmaceutically acceptable salting ion, methyl or ethyl, or a group of the sub-formula (b):

$$R_4CO— \qquad (b)$$

wherein $R_4$ is $R_5$ or $NHR_5$ wherein $R_5$ is alkyl of up to 6 carbon atoms, alkenyl of up to 6 carbon atoms, phenyl unsubstituted or substituted by alkyl of up to 3 carbon atoms, alkoxyl of up to 3 carbon atoms, chlorine or fluorine or alkyl of up to 6 carbon atoms substituted by phenyl or phenyloxy which itself is unsubstituted or nuclear substituted by alkyl of up to 3 carbon atoms, alkoxyl of up to 3 carbon atoms, chlorine or fluorine, with the proviso that when $R_2$ is a group of the formula (a) the compound has cis stereochemistry about the β-lactam ring, in combination with a pharmaceutically acceptable carrier.

39. A method according to claim 38 wherein $R_1$ is lower alkyl, benzyl, methylbenzyl, methoxylbenzyl, nitrobenzyl, halobenzyl or phthalidyl.

40. A method according to claim 38 wherein $R_1$ is an alkali or alkaline earth metal ion.

41. A method according to claim 38 wherein $R_2$ is a group of the sub-formula (a) when $R_3$ is an alkali or alkaline earth metal ion.

42. A method according to claim 38 wherein $R_2$ is hydrogen.

43. A method according to claim 38 wherein the compound is of the formula (VIII):

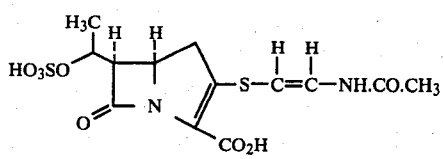

in the form of a pharmaceutically acceptable di-basic salt or of a pharmaceutically acceptable mono-basic salt of an in-vivo hydrolysable ester of the carboxylate group.

44. A method according to claim 38 wherein $R_4$ is $R_5$ wherein $R_5$ is alkyl of up to 6 carbon atoms, alkenyl of up to 6 carbon atoms, phenyl unsubstituted or substituted by alkyl of up to 3 carbon atoms, alkoxyl of up to 3 carbon atoms, chlorine or fluorine, or alkyl of up to 6 carbon atoms substituted by phenyl or phenyloxy which is unsubstituted or nuclear substituted by alkyl of up to 3 carbon atoms, alkoxyl of up to 3 carbon atoms, chlorine or fluorine.

45. A method according to claim 43 wherein the di-basic salt is the di-sodium or di-potassium salt and the mono-salt of an in-vivo hydrolyzable ester is the sodium or potassium salt of the phthalidyl ester.

46. A method according to claim 38 wherein the compound is benzyl (5R,6S)-3-[(Z)-2-acetamidoethenylthio]-6-[(S)-1-hydroxy-ethyl]-7-oxo-1-azabicyclo[3.2.0]-hept-2-ene-2-carboxylate.

47. A method according to claim 38 wherein the compound is p-nitrobenzyl (5R,6S)-3-[(Z)-2-acetamidoethenylthio]-6-[(S)-1-hydroxyethyl]-7-oxo-1-azabicyclo[3.2.0]hept-2-ene-2-carboxylate.

48. A method according to claim 38 wherein the compound is sodium (5R,6S)-3-[(Z)-2-acetamidoethenylthio]-6-[(S)-1-hydroxyethyl]-7-oxo-1-azabicyclo[3.2.0]-hept-2-ene-2-carboxylate.

49. A method according to claim 38 wherein the compound is p-nitrobenzyl (5R,6R)-3-[(Z)-2-acetamidoethenylthio]-6-[(S)-1-hydroxyethyl]-7-oxo-1-azabicyclo[3.2.0]-hept-2-ene-2-carboxylate.

50. A method according to claim 38 wherein the compound is sodium (5R,6R)-3-[(Z)-2-acetamidoethenylthio-6-[(S)-1-hydroxyethyl]-7-oxo-1-azabicyclo[3.2.0]hept-2-ene-2-carboxylate.

51. A method according to claim 38 wherein the compound is p-nitrobenzyl (5R,6R)-3-[(Z)-2-acetamidoethenylthio]-6-[(S)-1-ethoxysulphonyloxyethyl]-7-oxo-1-azabicyclo[3.2.0]hept-2-ene-2-carboxylate.

52. A method according to claim 38 wherein the compound is p-nitrobenzyl (5R,6R)-3-[(Z)-2-acetamidoethenylthio]-6-[(S)-1-sodiosulphatoethyl]-7-oxo-1-azabicyclo[3.2.0]hept-2-ene-2-carboxylate.

53. A method according to claim 38 wherein the compound is disodium (5R,6R)-3-[(Z)-2-acetamidoethenylthio]-6-[(S)-1-sulphatoethyl]-7-oxo-1-azabicyclo[3.2.0]hept-2-ene-2-carboxylate.

54. A method according to claim 38 wherein the administration is oral.

55. A method according to claim 38 wherein the administration is parenteral.

56. A method according to claim 38 wherein the administration is by topical application.

57. A method according to claim 38 wherein the bacterial infection to be treated is a respiratory infection.

58. A method according to claim 38 wherein the bacterial infection to be treated is one in the urinary tract.

59. A method according to claim 38 wherein the human or animal to be treated is cattle and the infection is mastititis.

60. A method according to claim 38 wherein the infection to be treated is one caused by *Staphylococcus aureus*.

61. A method according to claim 38 wherein the infection to be treated is one caused by *E.coli*.

62. A method according to claim 38 wherein the infection to be treated is one caused by *Klepsiella aerogenes*.

* * * * *